United States Patent [19]

Gaughan

[11] 4,137,066

[45] Jan. 30, 1979

[54] SULFOXIDE AND SULFONE THIAZOLIDINES, COMPOSITIONS THEREOF AND THEIR UTILITY AS HERBICIDE ANTIDOTES

[75] Inventor: Edmund J. Gaughan, Berkeley, Calif.

[73] Assignee: Stauffer Chemical Company, Westport, Conn.

[21] Appl. No.: 548,316

[22] Filed: Feb. 10, 1975

Related U.S. Application Data

[63] Continuation-in-part of Ser. No. 357,133, May 4, 1973, abandoned.

[51] Int. Cl.² ............................................. C07D 277/04
[52] U.S. Cl. ......................................... 71/91; 71/100; 71/118; 260/306.7 R
[58] Field of Search .................. 260/306.7 R, 301; 71/90, 91, 100, 118

[56] References Cited

FOREIGN PATENT DOCUMENTS

| | | | |
|---|---|---|---|
| 814536 | 11/1976 | Belgium | 260/306.7 |
| 1403876 | 8/1975 | United Kingdom | 260/306.7 |

OTHER PUBLICATIONS

Ratner et al., J.A.C.S., vol. 59, pp. 200–206 (1937).

Primary Examiner—Jose Tovar
Assistant Examiner—D. B. Springer
Attorney, Agent, or Firm—Harry A. Pacini

[57] ABSTRACT

Substituted sulfoxide and sulfone thiazolidine as new compositions and their utility in herbicidal compositions comprising an active herbicidal compound and an antidote therefor and the methods of use; the new compounds and antidote compounds correspond to compounds having the formula

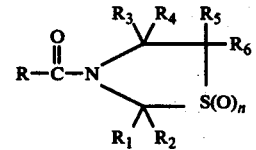

in which R is haloalkyl, alkyl, alkylthio; and $R_1$, $R_2$, $R_3$, $R_4$, $R_5$ and $R_6$ are independently selected from the group consisting of hydrogen, lower alkyl, alkoxyalkyl, and lower alkylol; and n is an integer having the value 1 or 2.

89 Claims, No Drawings

SULFOXIDE AND SULFONE THIAZOLIDINES, COMPOSITIONS THEREOF AND THEIR UTILITY AS HERBICIDE ANTIDOTES

This application is a continuation-in-part of copending application Ser. No. 357,133, filed May 4, 1973, now abandoned.

BACKGROUND OF THE INVENTION

Among the many herbicidal compounds commercially available, the thiocarbamates alone or admixed with other herbicides, such as the triazines, have reached a relatively high degree of commercial success. These herbicides are immediately toxic to a large number of weed pests at different concentrations varying with the resistance of the weed pests. Some examples of these compounds are described and claimed in U.S. Pat. Nos. 2,913,327, 3,037,853, 3,175,897, 3,185,720, 3,198,786 and 3,582,314. It has been found in practice that the use of these thiocarbamates as herbicides on crops sometimes causes serious injuries to the crop plant. Also of particular interest are the substituted acetanilide herbicides. When used in the recommended amounts in the soil to control many broadleaf weeds and grasses, serious malformation and stunting of the crop plants result. This abnormal growth in the crop plants results in loss of crop yield. Previous attempts to overcome this problem involve the treatment of the crop seed with certain antagonistic agents prior to planting, see U.S. Pat. Nos. 3,131,509 and 3,564,768. These antagonistic agents have not been notably successful. The aforementioned patent specifically exemplifies the treatment of seeds employing compounds of a different chemical class not suggestive of the present invention.

Description of the Invention

It has been discovered that plants can be protected against injury by the thiocarbamate-type and substituted acetanilide-type herbicides, alone or mixed with other compounds and/or the tolerance of the plants can be substantially increased to the active compounds of the above-noted U.S. Patents by adding to the soil an antidote compound corresponding to the following formula:

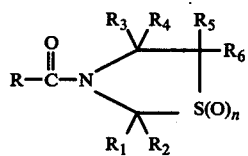

in which R is haloalkyl, alkyl or alkylthio; and $R_1$, $R_2$, $R_3$, $R_4$, $R_5$ and $R_6$ are independently selected from the group consisting of hydrogen, lower alkyl, alkoxyalkyl and lower alkylol; and n is an integer having the value 1 or 2.

In the above description, the following embodiments are intended for the various substituent groups: For R, haloalkyl and alkyl preferably includes, unless otherwise provided for, those members which contain from 1 to 10 carbon atoms, inclusive, in both straight chain and branched chain configurations, and the term halo includes chloro and bromo as mono, di, tri, tetra and per substitutions. As exemplary of the alkyl portion within the preferred embodiment are the following: methyl, ethyl, n-propyl, isopropyl, n-butyl, sec.-butyl, 1,1-dimethylbutyl, amyl, isoamyl, 2,4,4-trimethylpentyl, n-hexyl, isohexyl, n-heptyl, n-octyl, isooctyl, nonyl, and decyl. The term alkylthio preferably includes those members which contain from 1 to 4 carbon atoms, inclusive, for example, methylthio, ethylthio, n-propylthio, isopropylthio, n-butylthio, t-butylthio, and the like. For $R_1$, $R_2$, $R_3$, $R_4$, $R_5$ and $R_6$, the term lower alkyl preferably includes, unless otherwise provided for, those members which contain from 1 to 4 carbon atoms, inclusive, for example, methyl, ethyl, n-propyl, isopropyl, n-butyl, sec.-butyl, tert.-butyl, and the like. The term alkoxyalkyl preferably includes those members having a total of 2 to 4 carbon atoms, inclusive, for example, methoxymethyl, methoxyethyl, ethoxyethyl, ethoxymethyl and the like. The term lower alkylol preferably includes those members having 1 to 4 carbon atoms, inclusive, for example, methylol, ethylol, propylol and butylol.

As an alternative mode of action, the compounds of this invention may interfere with the normal herbicidal action of the thiocarbamate-type and other herbicides to render them selective in their action. Whichever mode of action is present, the corresponding beneficial and desirable effect is the continued herbicidal effect of the thiocarbamate or substituted acetanilide with the accompanying decreased herbicidal effect on desired crop species. This advantage and utility will become more apparent hereinafter.

Therefore, the terms herbicide antidote or antidotal amount, are meant to describe that effect which tends to counteract the normal injurious herbicidal response that the herbicide might otherwise produce. Whether it is to be termed a remedy, interferant, protectant, or the like, will depend upon the exact mode of action. The mode of action is varied, but the effect, which is desirable, is the result of the method of treating the soil in which a crop is planted. Hitherto, there have been no systems which have been satisfactory for this purpose.

The compounds of this invention represented by the above formula can be prepared by several different procedures depending upon the starting materials.

The thiazolidine intermediates were prepared by the condensation of the amino mercaptan with a suitable aldehyde or ketone in boiling benzene with the continuous separation of water. This method is described by Bergmann et al., JACS 75 358 (1953). Usually, the thiazolidine intermediates were pure enough to be used directly without further purification. Aliquots of these solutions were then used to prepare the unoxidized intermediates of the compounds of this invention. The appropriate unoxidized intermediate was reacted with an acid chloride in the presence of a hydrogen chloride acceptor, such as triethylamine, to prepare the desired compound. Workup and purification procedures for the unoxidized intermediates involved standard methods of extraction, distillation or crystallization.

The compounds represented by the above formula can be prepared by mixing together an appropriate thiazolidine with a stoichiometric amount of oxidizing agent. That is, if the sulfoxide is desired, then at least one molar equivalent of oxidizing agent to thiazolidine is employed. If the sulfone is desired, then at least two molar equivalents of oxidizing agent to thiazolidine is employed. The preferred oxidizing agent is m-chloro perbenzoic acid. A solvent can be used if desired. The use of a solvent will facilitate the reaction and assist in adding the oxidizing agent and handling of the product in the work-up procedure. After the reaction is complete, the end product is readily recovered by normal work-up procedures, such as crystallization, sublimation or distillation.

The compounds of the present invention and their preparation are more particularly illustrated by the following examples. Following the examples of preparation is a table of compounds which can be prepared according to the procedures described herein.

EXAMPLE I

Preparation of Intermediate: 2,2-dimethyl-3-dichloroacetyl thiazolidine.

Four and seven-tenths (4.7 g.) grams of 2,2-dimethyl thiazolidine and 4.5 g. of triethylamine were dissolved in 50 ml. of methylene chloride and 5.9 g. of dichloroacetyl chloride was added dropwise with stirring. The mixture was cooled in a water bath at room temperature.

When reaction was complete, the mixture was poured into water and the solvent layer separated, dried over anhydrous magnesium sulfate, and the solvent removed under vacuum. Yield was 3.6 g. of a waxy solid. Recrystallization of another sample from diethyl ether gave a white solid, m.p. 109°–111° C.

EXAMPLE II

Preparation of 3-(dichloroacetyl)-2,2-dimethyl-1,3-thiazolidine sulfone.

To 4.6 g. (0.02 mole) of the thiazolidine prepared as in Example I, in 50 ml. of methylene chloride is added a solution of 7.2 g. (0.042 mole) of m-chloroperbenzoid acid in 100 ml. of the same solvent at a temperature of 5°–10° C. The reaction mixture is stirred at room temperature for one hour and then at reflux temperature for one hour. The reaction mixture is cooled to 5° C. and filtered cold. The filter-cake is washed with 5 ml. of methylene chloride. The filtrate is washed twice with 30 ml. of sodium carbonate solution and twice with water. The filtrate is dried over magnesium sulfate. The solvent is removed in vacuo. There is obtained 3.8 g. of the title compound, a white solid, m.p. 144°–149° C. Infrared analysis supports the expected structure.

EXAMPLE III

Preparation of 3-(dichloroacetyl)-2,2-dimethyl-1,3-thiazolidine sulfoxide.

To 6.8 g. (0.03 mole) of the thiazolidine prepared as in Example I, in 70 ml. of methylene chloride is added a solution of 5.5 g. (0.032 mole) of m-chloroperbenzoic acid in 80 ml. of methylene chloride at −15° C. A precipitate gradually appears. The reaction mixture is stirred for 1.5 hours at room temperature, then cooled to about 5°–10° C. and filtered. The filtrate is washed twice with sodium carbonate solution, once with water, and dried. The solvent is removed in vacuo. There is obtained 5.3 g. of the title compound, m.p. 105°–113° C. Infrared analysis supports the expected structure.

TABLE I

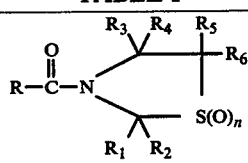

| COMPOUND NUMBER | R | $R_1$ | $R_2$ | $R_3$ | $R_4$ | $R_5$ | $R_6$ | n |
|---|---|---|---|---|---|---|---|---|
| 1 | $CHCl_2$ | $CH_3$ | $CH_3$ | H | H | H | H | 2 |
| 2 | $CHCl_2$ | $CH_3$ | $CH_3$ | H | H | H | H | 1 |
| 3 | $CH_2Cl$ | $CH_3$ | $CH_3$ | H | H | H | H | 2 |
| 4 | $CHCl_2$ | $CH_3$ | $CH_3$ | H | H | $CH_3$ | H | 2 |
| 5 | $CHCl_2$ | $CH_3$ | $CH_3$ | H | H | $CH_3$ | H | 1 |
| 6 | $CHCl_2$ | $C_2H_5$ | H | H | H | H | H | 2 |
| 7 | $CH_2Cl$ | $C_2H_5$ | H | H | H | H | H | 1 |
| 8 | $CH_2Cl$ | $C_2H_5$ | H | H | H | H | H | 2 |
| 9 | $CHCl_2$ | $C_2H_5$ | H | H | H | $CH_3$ | H | 1 |
| 10 | $CHCl_2$ | $C_2H_5$ | H | H | H | $CH_3$ | H | 2 |
| 11 | $CH_3CCl_2$ | $CH_3$ | $CH_3$ | H | H | H | H | 2 |
| 12 | $CH_3CCl_2$ | $CH_3$ | $CH_3$ | H | H | H | H | 1 |
| 13 | $CH_2BrCHBr$ | $C_2H_5$ | H | H | H | H | H | 2 |
| 14 | $CH_2BrCHBr$ | $C_2H_5$ | H | H | H | H | H | 1 |
| 15 | $CH_2ClCH_2$ | $CH_3$ | $CH_3$ | H | H | H | H | 2 |
| 16 | $CH_2ClCH_2$ | $CH_3$ | $CH_3$ | H | H | H | H | 1 |
| 17 | $CH_2Cl$ | $CH_3$ | $CH_3$ | H | H | H | H | 1 |
| 18 | $CHCl_2$ | $C_2H_5$ | H | H | H | H | H | 1 |
| 19 | $CH_2BrCHBr$ | $CH_3$ | $t-C_4H_9$ | H | H | H | H | 2 |
| 20 | $CH_2BrCHBr$ | $CH_3$ | $t-C_4H_9$ | H | H | H | H | 1 |
| 21 | $CHCl_2$ | $CH_3$ | $t-C_4H_9$ | H | H | H | H | 2 |
| 22 | $CHCl_2$ | $CH_3$ | $t-C_4H_9$ | H | H | H | H | 1 |
| 23 | $CHCl_2$ | H | H | $CH_3$ | $CH_3$ | H | H | 2 |
| 24 | $CHCl_2$ | H | H | $CH_3$ | $CH_3$ | H | H | 1 |
| 25 | $CHCl_2$ | $CH_3OCH_2$ | H | H | H | H | H | 2 |
| 26 | $CHCl_2$ | $CH_3OCH_2$ | H | H | H | H | H | 1 |
| 27 | $CHBr_2$ | $C_2H_5$ | H | H | H | H | H | 2 |
| 28 | $CHBr_2$ | $C_2H_5$ | H | H | H | H | H | 1 |
| 29 | $CCl_3$ | $CH_3$ | $CH_3$ | H | H | H | H | 2 |
| 30 | $CCl_3$ | $CH_3$ | $CH_3$ | H | H | H | H | 1 |
| 31 | $CHBr_2$ | $CH_3$ | $CH_3$ | H | H | H | H | 2 |
| 32 | $CHBr_2$ | $CH_3$ | $CH_3$ | H | H | H | H | 1 |
| 33 | $CH_3CHBr$ | $CH_3$ | $CH_3$ | H | H | H | H | 2 |
| 34 | $CH_3CHBr$ | $CH_3$ | $CH_3$ | H | H | H | H | 1 |
| 35 | $CHCl_2$ | H | H | H | H | H | H | 2 |
| 36 | $CHCl_2$ | H | H | H | H | H | H | 1 |
| 37 | $CHCl_2$ | $CH_3$ | $CH_3$ | $CH_3$ | $CH_2OH$ | H | H | 2 |
| 38 | $CHCl_2$ | $CH_3$ | $CH_3$ | $CH_3$ | $CH_2OH$ | H | H | 1 |

TABLE I-continued

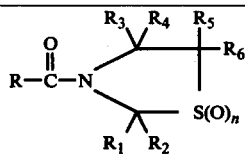

| COMPOUND NUMBER | R | $R_1$ | $R_2$ | $R_3$ | $R_4$ | $R_5$ | $R_6$ | n |
|---|---|---|---|---|---|---|---|---|
| 39 | $CHCl_2$ | $C_2H_5$ | H | $C_2H_5$ | H | H | H | 2 |
| 40 | $CHCl_2$ | $C_2H_5$ | H | $C_2H_5$ | H | H | H | 1 |
| 41 | $C_6H_{13}$ | $CH_3$ | $CH_3$ | H | H | H | H | 2 |
| 42 | $C_6H_{13}$ | $CH_3$ | $CH_3$ | H | H | H | H | 1 |
| 43 | $CH_3$ | $CH_3$ | $CH_3$ | $C_2H_5$ | H | H | H | 2 |
| 44 | $CH_3$ | $CH_3$ | $CH_3$ | $C_2H_5$ | H | H | H | 1 |
| 45 | $n-C_3H_7$ | $CH_3$ | $CH_3$ | $C_2H_5$ | H | H | H | 2 |
| 46 | $n-C_3H_7$ | $CH_3$ | $CH_3$ | $C_2H_5$ | H | H | H | 1 |
| 47 | $CH_2BrCH_2$ | $CH_3$ | $CH_3$ | H | H | H | H | 2 |
| 48 | $CH_2BrCH_2$ | $CH_3$ | $CH_3$ | H | H | H | H | 1 |
| 49 | $CH_2BrCHBr$ | $CH_3$ | $CH_3$ | H | H | H | H | 2 |
| 50 | $CH_2BrCHBr$ | $CH_3$ | $CH_3$ | H | H | H | H | 1 |
| 51 | $CH_2Br$ | H | H | H | H | H | H | 2 |
| 52 | $CH_2Br$ | H | H | H | H | H | H | 1 |
| 53 | $CH_3CHBr$ | H | H | H | H | H | H | 2 |
| 54 | $CH_3CHBr$ | H | H | H | H | H | H | 1 |
| 55 | $CH_2BrCH_2$ | H | H | H | H | H | H | 2 |
| 56 | $CH_2BrCH_2$ | H | H | H | H | H | H | 1 |
| 57 | $CH_2BrCHBr$ | H | H | H | H | H | H | 2 |
| 58 | $CH_2BrCHBr$ | H | H | H | H | H | H | 1 |
| 59 | $CH_3C(CH_3)Br$ | H | H | H | H | H | H | 2 |
| 60 | $CH_3C(CH_3)Br$ | H | H | H | H | H | H | 1 |
| 61 | $ClCH_2CH_2CH_2-$ | $CH_3$ | $CH_3$ | H | H | H | H | 2 |
| 62 | $ClCH_2CH_2CH_2$ | $CH_3$ | $CH_3$ | H | H | H | H | 1 |
| 63 | $CH_3CHClCH_2$ | $CH_3$ | $CH_3$ | H | H | $CH_3$ | H | 2 |
| 64 | $CH_3CHClCH_2$ | $CH_3$ | $CH_3$ | H | H | $CH_3$ | H | 1 |
| 65 | $C_2H_5CHBr$ | $CH_3$ | $CH_3$ | H | H | H | H | 2 |
| 66 | $C_2H_5$ | $CHBr$ | $CH_3$ | H | H | H | H | 1 |
| 67 | $C_3H_7CHBr$ | $CH_3$ | $CH_3$ | H | H | H | H | 2 |
| 68 | $C_3H_7CHBr$ | $CH_3$ | $CH_3$ | H | H | H | H | 1 |
| 69 | $CH_2Br(CH_2)_4$ | $CH_3$ | $CH_3$ | H | H | H | H | 2 |
| 70 | $CH_2Br(CH_2)_4$ | $CH_3$ | $CH_3$ | H | H | H | H | 1 |
| 71 | $CHCl_2$ | H | H | H | H | H | H | 2 |
| 72 | $CHCl_2$ | H | H | H | H | H | H | 1 |
| 73 | $CHCl_2$ | $CH_3$ | $CH_3$ | $C_2H_5$ | H | H | H | 2 |
| 74 | $CHCl_2$ | $CH_3$ | $CH_3$ | $C_2H_5$ | H | H | H | 1 |
| 75 | $CHCl_2$ | $CH_3$ | $C_2H_5$ | H | H | H | H | 2 |
| 76 | $CHCl_2$ | $CH_3$ | $C_2H_5$ | H | H | H | H | 1 |
| 77 | $CHCl_2$ | H | H | $C_2H_5$ | H | H | H | 2 |
| 78 | $CHCl_2$ | H | H | $C_2H_5$ | H | H | H | 1 |

The compounds of this invention can be employed in effective herbicidal antidote compositions comprising thiocarbamates or substituted acetanilides in combination with antidote compounds described hereinabove. They are tested in the following manner.

Seed Treatment Test

Small flats are filled with Felton loamy sand soil. Soil incorporated herbicides are applied at this time. The soil from each flat is placed into a five-gallon cement mixer where the soil is mixed, as the herbicides are applied using a pre-determined amount of a stock solution. For EPTAM®, the stock solution contains the equivalent of active ingredient such that one milliliter of stock solution is applied to the soil for each pound of herbicide desired. One ml. of stock solution contains 7 mg. of herbicide which equals one pound per acre when applied to the soil in the flats. For LASSO®, the stock solution contains the equivalent of active ingredient, such that one milliliter of stock solution when applied to soil is equivalent to one-half pound of the herbicide. Therefore, one milliliter of stock solution contains 2.05 mg. (a.i.) of herbicide which equals one-half pound per acre. After the herbicide incorporation, the soil is placed back into the flats.

Flats of herbicide-treated and untreated soil are then ready to be planted. A pint sample of soil is removed from each flat and placed next to each flat for later use in covering up the seeds. The soil is leveled and rows one-half inch deep are made for planting seeds. Alternating rows of treated and untreated crop seeds are sown. In each test, six PAG 344T field corn seeds are planted in each row. Rows are approximately 1½ inches apart in the flat. Seeds are treated by placing 50 mg. of the antidote compound with 10 grams of corn seed (0.05% w/w) in a suitable container and shaking them until the seeds are uniformly covered with the compound. Antidote compounds are also applied as liquid slurries and powders or dusts. In some cases, acetone is used to dissolve powdered or solid compounds so they could be more effectively applied to the seeds.

After the flats are seeded, they are covered with the one pint of soil which has been removed just prior to planting. Flats are placed on greenhouse benches where temperatures ranged from 70°-90° F. Flats are watered by sprinkling as needed to assure good plant growth. Percent control ratings are taken two, three and four weeks after the treatments are applied.

In each test, the herbicide is applied alone, in combination with the seed protectant, and the seed protectant is applied alone to check for phytotoxicity. The degree of the effect was noted by comparison with the control.

When used with S-ethyl dipropyl-thiocarbamate (EPTC 6E) at 0.5 lb/A., Compound Number 1 as an 0.5% seed treatment on barley gave 80% protection from injury to the growing barley. Similarly, Compound Number 1 with EPTC at 0.5 lb/A. gave approximately 80% protection to milo (sorghum) when applied as an 0.5% seed treatment.

When used with 2-chloro-2',6'-diethyl-N-(methoxymethyl) acetanilide at 2 lb/A., Compound Number 1 protected milo (sorghum) by about 86% when applied as an 0.5% seed treatment. Under the same test procedure as a seed treatment, wheat was protected about 37.5%.

Procedure: Multicrop Antidote Screen

Plastic flats are filled with loamy sand soil. Since a variety of grass and broadleaf crops were used in these tests, EPTAM ® (EPTC) was incorporated at ½ and 5 lb/A., while a constant rate of 5 lb/A. of the additive was used. LASSO ® (2-chloro-2',6'-diethyl-N-(methoxymethyl)acetanilide, EPTAM ® (EPTC) and the herbicide antidote were applied separately by pipetting measured amounts of the appropriate stock solutions into the soil during incorporation in a 5 gallon rotary cement mixer. Stock solutions were prepared as follows:

A. ½ lb/A.: 670 mg. of EPTC 6E (75.5% a.i.) is diluted with 500 ml. of deionized water so that 2 ml. equals ½ lb/A. flat.
B. 5 lb/A.: 6700 mg. of EPTC 6E (75.5%) is diluted with 500 ml. of deionized water so that 2 ml. equals 5 lb/A. flat.
C. 2 lb/A.: 427 mg. LASSO 4E is diluted with 100 ml. of deionized water so that 1 ml. equals 2.05 mg. (a.i.) and 4 ml. equals 8.2 mg. equivalent to 2 lb/A. flat.

Antidote stock solutions are prepared by diluting 102 mg. of technical material with 10 ml. of acetone 1% Tween 20 ® (polyoxyethylene sorbitan monolaurate) so that 2 ml. equals 5 lb/A flat.

After the soil is treated with both herbicide and additive, the soil is transferred from the mixer back into the flat where it is then prepared for seeding. The initial step in preparation is to remove a one pint sample of soil from each flat to be retained and used to cover the seeds after planting. The soil is then leveled and rows one-quarter inch deep are made in each flat. Flats treated with 5 lb/A. of EPTAM are seeded to DeKalb XL-44 corn (Zea maize), US H9 sugarbeets (Beta vulgare), small seeded gray striped sunflower (*Helianthus annus*), Acala cotton (*Gossypium hirsutum*), Brag soybeans (*Glycine max*) and oilseed rape (*Brassica napus*). Flats treated with ½ lb/A. of EPTAM are seeded to red oats (*Avena byzantina*), R-10 milo (*Sorghum vulgare*), Fremont HRS wheat (*Triticum aestivum*), giant foxtail (*Seteria feberii*), Calrose rice (*Oryza sativa*) and Blue Mariate barley (*Hordeum vulgare*). Seeds are then covered with the pint soil sample removed prior to seeding.

The flats are then placed on greenhouse benches where temperatures are maintained between 70°-90° F. The soil is watered by sprinkling to assure good plant growth.

Injury ratings are taken 2 and 4 weeks after the treatments are applied. Soil treated with the herbicides alone at ½, 2 or 5 lb/A. is included to provide a basis for determining the amount of injury reduction provided by the herbicide antidotes. The percent protection is determined by a comparison with flats not treated with the candidate antidote.

At 0.5 lb/A. of EPTC and 5.0 lb/A. of Compound No. 1, after two weeks, milo (sorghum) was afforded 100% protection; wheat, 57% protection; and barley, 25% protection. At 5.0 lb/A. of EPTC and 5.0 lb/A. of Compound No. 1, corn was afforded 100% protection. Compound No. 1, applied at 1 lb/A. pre-plant incorporated, reduced injury to milo (sorghum) and wheat by about 60% and 80%, respectively, with 2 lb/A. of LASSO. These results were observed at the 2 week rating. Compound No. 2 (sulfoxide) showed 100% protection of corn (DeKalb XL-44) when tested at 0.05 lb/A. with 5.0 lb/A. of EPTC. In the test with barley at 0.5 lb/A. of EPTC and 5 lb/A. of Compound No. 2, 80% protection was observed.

In-Furrow Application Antidote Screen

Flats were filled with loamy sand soil. VERNAM ® (S-propyl dipropylthiocarbamate), a thiocarbamate herbicide, and the candidate antidotes were applied separately. The herbicide was applied by pipetting a measured amount of an appropriate stock solution into the soil during incorporation in a rotary mixer. Stock solutions were prepared as follows:

VERNAM ® 5 lb/A.: 3166 mg. of 6E (75% a.i.) was diluted with 500 ml. deionized water so that 4 ml. equals 5 lb/A. (20 mg. a.i./flat).

Antidote: Prepared by diluting 95 mg. of the compound with 15 ml. of acetone and 1% Tween 20 ® (polyoxyethylene sorbitan monolaurate) such that 1.5 ml. sprayed into the open furrows equals 5 lb/A. (based on the surface area of one-half the flat).

Application of the additive antidote was made in-furrow on the exposed seed before covering to achieve a planted state. Flats were seeded, for example, with DeKalb XL-44 corn (*Zea maize*).

After seeding, the flats were sectioned into two equal portions using a wooden barrier. One and one-half milliliters of antidote additive stock solution was atomized directly onto the exposed seed and into the furrow in one-half of the flat. The untreated section of the flat served as an herbicide check. The seeds were then covered with the one pint sample of soil removed earlier.

After the treated seeds were covered, the flats were placed on greenhouse benches where temperatures were maintained between 70°-90° F. The soil was watered by sprinkling to assure good plant growth.

Injury ratings were taken 2 weeks after treatments were applied. Individual flats treated with the herbicide alone at 5.0 lb/A. were included to provde a basis for determining the amount of injury reduction provided by the herbicide antidotes.

TABLE II

Per Cent Protection to Corn from VERNAM ® (5 lb/A.); In-Furrow Application

| Antidote (5 lb/A.) COMPOUND NUMBER | 2 Weeks |
| --- | --- |
| 1 | 100** |
| 2 | 100** |
| 3 | 78 |
| 4 | 89 |
| 5 | 89 |
| 6 | 100 |
| 7 | 100 |
| 8 | 78 |
| 9 | 89 |
| 10 | 78 |
| 11 | 0 |
| 12 | 33 |
| 13 | 78 |
| 14 | 56 |
| 15 | 56 |
| 16 | 33 |
| VERNAM* | 90 |

TABLE II-continued

Per Cent Protection to Corn from VERNAM ® (5 lb/A.); In-Furrow Application

Antidote (5 lb/A.)

| COMPOUND NUMBER | 2 Weeks |
|---|---|
|  | 95** |

** = 4 week data
* = per cent injury VERNAM ® at 5 lb/A.

Compounds 6 and 8 also exhibited 40 percent protection of barley at 5 lb/A. when applied with VERNAM ® at 1 lb/A. Compound 6 also provided 40 percent protection of wheat when applied at 5 lb/A. with VERNAM ® at 1 lb/A.

The antidote compounds and compositions of the present invention can be used in any convenient form. Thus, the antidote compounds can be formulated into emulsifiable liquids, emusifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not affect the herbicidal activity of the herbicides.

The amount of antidote compound present can range between about 0.01 to about 15 parts by weight of antidote compound described herein per each part by weight of herbicide. The exact amount of antidote compound will usually be determined on economic ratios for the most effective amount usable. It is understood that a non-phytotoxic quantity of antidote compound will be employed in the herbicidal compositions described herein.

The herbicides indicated in the tables and elsewhere are used at rates which produce effective control of undesirable vegetation. The rates are within the recommended amounts set forth by the supplier. Therefore, the weed control in each instance is commercially acceptable within the desired or recommended amount.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention the prevention of injury to a desired crop species in the presence of a specific compound or combination may be achieved. The beneficial plant species which can be protected by this method is not intended to be limited by the specific crops employed in the examples.

The herbicidal compounds employed in the utility of this invention are active herbicides of a general type. That is, the members of the classes are herbicidally effective against a wide range of plant species with no discrimination between desirable and undesirable species. The method of controlling vegetation comprises applying an herbicidally effective amount of the herein-described herbicidal compounds to the area or plant locus where control is desired. The compositions as set forth in this invention include those wherein the preferred active herbicidal compound is selected from EPTC, S-ethyl diisobutyl thiocarbamate, S-propyl dipropyl thiocarbamate, S-2,3,3-trichloroallyl-diisopropyl thiocarbamate, S-ethyl cyclohexyl ethyl thiocarbamate, S-ethyl hexahydro-1H-azepine-1-carbothioate, 2-chloro-N-isopropylacetanilide, N,N-diallyl-2-chloroacetamide, S-4-chlorobenzyl diethyl thiocarbamate, 2-chloro-4-ethylamino-6-isopropylamino-s-triazine, 2-chloro-4,6-bis(ethylamino)-s-triazine, 2(4-chloro-6-ethylamine-s-triazine-2-yl-amino)-2-methyl-propionitrile, 2-chloro-4-cyclopropylamino-6-isopropylamino-s-triazine, 2,4-dichlorophenoxyacetic acid, its esters and salts, and 3-(3,4-dichlorophenyl)-1,1-dimethylurea and combinations thereof.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants" it is meant germinant seeds, emerging seedlings, and established vegetation, including the roots and above-ground portions.

What is claimed is:

1. A compound having the formula

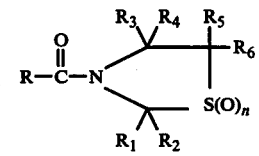

in which R is haloalkyl having 1 to 10 carbon atoms, inclusive, and having 1-3 chloro groups or 1-2 bromo groups, n is 2, $R_1$ is lower alkyl having 1 to 4 carbon atoms, inclusive, $R_2$ is lower alkyl having 1 to 4 carbon atoms, inclusive, and $R_3$, $R_4$, $R_5$ and $R_6$ are each hydrogen.

2. A compound according to claim 1 in which R is dichloromethyl, $R_1$ is methyl, and $R_2$ is methyl and n is 2.

3. A compound according to claim 1 in which R is chloromethyl, $R_1$ is methyl, $R_2$ is methyl and n is 2.

4. A compound according to claim 1 in which R is 1,1-dichloroethyl, $R_1$ is methyl, $R_2$ is methyl and n is 2.

5. A compound according to claim 1 in which R is 2-chloroethyl, $R_1$ is methyl, $R_2$ is methyl and n is 2.

6. A compound having the formula

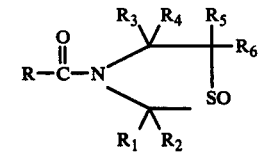

in which R is haloalkyl having 1 to 10 carbon atoms, inclusive, and having 1-3 chloro groups or 1-2 bromo groups, $R_1$ is lower alkyl having 1 to 4 carbon atoms, inclusive, $R_2$ is lower alkyl having 1 to 4 carbon atoms, inclusive, and $R_3$, $R_4$, $R_5$ and $R_6$ are each hydrogen.

7. A compound according to claim 6 in which R is dichloromethyl, $R_1$ is methyl, $R_2$ is methyl and n is 1.

8. A compound according to claim 6 in which R is 1,1-dichloroethyl, $R_1$ is methyl, $R_2$ is methyl and n is 1.

9. A compound according to claim 6 in which R is 2-chloroethyl, $R_1$ is methyl, $R_2$ is methyl and n is 1.

10. A compound having the formula

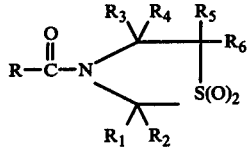

in which R is haloalkyl containing 1 to 10 carbon atoms, inclusive, $R_1$ is lower alkyl containing 1 to 4 carbon atoms, inclusive, $R_2$ is lower alkyl containing 1 to 4 carbon atoms, inclusive, $R_5$ is lower alkyl containing 1 to 4 carbon atoms, inclusive, $R_3$, $R_4$ and $R_6$ are each hydrogen.

11. A compound according to claim 10 in which R is dichloromethyl, $R_1$ is methyl, $R_2$ is methyl, $R_5$ is methyl and n is 2.

12. A compound having the formula

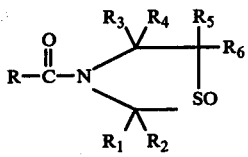

in which R is haloalkyl containing 1 to 10 carbon atoms, inclusive, $R_1$ is lower alkyl containing 1 to 4 carbon atoms, inclusive, $R_3$, $R_4$, $R_5$ and $R_6$ are each hydrogen.

13. A compound according to claim 12 in which R is dichloromethyl, $R_1$ is methyl, $R_2$ is methyl and n is 1.

14. A compound having the formula

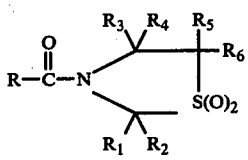

in which R is haloalkyl having 1 to 10 carbon atoms, inclusive, and having 1–3 chloro groups or 1–2 bromo groups, $R_1$ is lower alkyl having 1 to 4 carbon atoms, inclusive, $R_2$, $R_3$, $R_4$, $R_5$ and $R_6$ are each hydrogen.

15. A compound according to claim 14 in which R is dichloromethyl, $R_1$ is ethyl, $R_2$ is hydrogen and n is 2.

16. A compound according to claim 14 in which R is chloromethyl, $R_1$ is ethyl, $R_2$ is ethyl and n is 2.

17. A compound according to claim 14 in which R is 1,2-dibromoethyl, $R_1$ is ethyl, $R_2$ is hydrogen and n is 2.

18. A compound having the formula

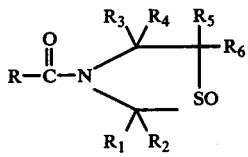

in which R is haloalkyl having 1 to 10 carbon atoms, inclusive, and having 1–3 chloro groups or 1–2 bromo groups, $R_1$ is lower alkyl having 1 to 4 carbon atoms, inclusive, $R_2$, $R_3$, $R_4$, $R_5$ and $R_6$ are each hydrogen.

19. A compound according to claim 18 in which R is dichloromethyl, $R_1$ is ethyl, $R_2$ is hydrogen and n is 1.

20. A compound according to claim 18 in which R is 1,2-dibromoethyl, $R_1$ is ethyl, $R_2$ is hydrogen and n is 1.

21. A compound having the formula

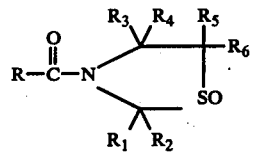

in which R is haloalkyl having 1 to 10 carbon atoms, inclusive, and having 1–3 chloro groups or 1–2 bromo groups, $R_1$ is lower alkyl having 1 to 4 carbon atoms, inclusive, $R_5$ is lower alkyl having 1 to 4 carbon atoms, inclusive, and $R_2$, $R_3$, $R_4$ and $R_6$ are each hydrogen.

22. A compound according to claim 21 in which R is dichloromethyl, $R_1$ is ethyl, $R_2$ is hydrogen, $R_5$ is methyl and n is 1.

23. A compound having the formula

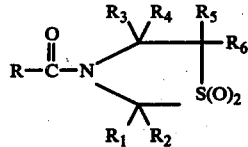

in which R is haloalkyl having 1 to 10 carbon atoms, inclusive, and having 1–3 chloro groups or 1–2 bromo groups, $R_1$ is lower alkyl having 1 to 4 carbon atoms, inclusive, $R_5$ is lower alkyl having 1 to 4 carbon atoms, inclusive, and $R_2$, $R_3$, $R_4$ and $R_6$ are each hydrogen.

24. A compound according to claim 23 in which R is dichloromethyl, $R_1$ is ethyl, $R_2$ is hydrogen, $R_5$ is methyl and n is 2.

25. In the method of controlling weeds wherein a thiocarbamate herbicide is applied to the habitat of said weeds, the improvement comprising applying to the habitat thereof from about 0.01 to about 15 parts by weight for each part by weight of the thiocarbamate herbicide an antidote compound corresponding to the formula

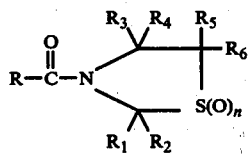

in which R is haloalkyl having 1 to 10 carbon atoms, inclusive, and having 1–3 chloro groups or 1–2 bromo groups, having 1 to 10 carbon atoms, inclusive, and $R_1$, $R_2$, $R_3$, $R_4$, $R_5$ and $R_6$ are independently selected from the group consisting of hydrogen, lower alkyl containing 1 to 4 carbon atoms, inclusive, alkyoxyalkyl having a total of 2 to 4 carbon atoms, inclusive, and n is an integer having the value 1 or 2.

26. In the method according to claim 25 in which said antidote compound has the formula wherein R is haloalkyl having 1 to 10 carbon atoms, inclusive, $R_1$ is lower alkyl having 1 to 4 carbon atoms, inclusive, $R_2$ is lower alkyl having 1 to 4 carbon atoms, inclusive, and $R_3$, $R_4$, $R_5$ and $R_6$ are each hydrogen and n is 2.

27. In the method of claim 26 in which R is dichloromethyl, $R_1$ is methyl, $R_2$ is methyl and n is 2.

28. In the method of claim 26 in which R is chloromethyl, $R_1$ is methyl, $R_2$ is methyl and n is 2.

29. In the method of claim 26 in which R is 1,1-dichloroethyl, $R_1$ is methyl, $R_2$ is methyl and n is 2.

30. In the method of claim 26 in which R is 2-chloroethyl, $R_1$ is methyl, $R_2$ is methyl and n is 2.

31. In the method according to claim 25 in which said antidote compound has the formula wherein R is haloalkyl, $R_1$ is lower alkyl, $R_2$ is lower alkyl and $R_3$, $R_4$, $R_5$ and $R_6$ are each hydrogen and n is 1.

32. In the method of claim 31 in which R is dichloromethyl, $R_1$ is methyl, $R_2$ is methyl and n is 1.

33. In the method of claim 31 in which R is 1,1-dichloroethyl, $R_1$ is methyl, $R_2$ is methyl and n is 1.

34. In the method of claim 31 in which R is 2-chloroethyl, $R_1$ is methyl, $R_2$ is methyl and n is 1.

35. In the method according to claim 25 in which said antidote compound has the formula wherein R is haloalkyl, $R_1$ is lower alkyl, $R_2$ is lower alkyl, $R_5$ is lower alkyl, $R_3$, $R_4$ and $R_6$ are each hydrogen and n is 2.

36. In the method of claim 35 in which R is dichloromethyl, $R_1$ is methyl, $R_2$ is methyl, $R_5$ is methyl and n is 2.

37. In the method according to claim 25 in which said antidote compound has the formula wherein R is haloalkyl, $R_1$ is lower alkyl, $R_2$ is lower alkyl, $R_3$, $R_4$, $R_5$ and $R_6$ are each hydrogen and n is 1.

38. In the method of claim 37 in which R is dichloromethyl, $R_1$ is methyl, $R_2$ is methyl and n is 1.

39. In the method according to claim 25 in which said antidote compound has the formula wherein R is haloalkyl, $R_1$ is lower alkyl, $R_2$, $R_3$, $R_4$, $R_5$ and $R_6$ are each hydrogen and n is 2.

40. In the method of claim 39 in which R is dichloromethyl, $R_1$ is ethyl, $R_2$ is hydrogen and n is 2.

41. In the method of claim 39 in which R is chloromethyl, $R_1$ is ethyl, $R_2$ is ethyl and n is 2.

42. In the method of claim 39 in which R is 1,2-dibromoethyl, $R_1$ is ethyl, $R_2$ is hydrogen and n is 2.

43. In the method according to claim 25 in which said antidote compound has the formula wherein R is haloalkyl, $R_1$ is lower alkyl, $R_2$, $R_3$, $R_4$, $R_5$ and $R_6$ are each hydrogen and n is 1.

44. In the method of claim 43 in which R is dichloromethyl, $R_1$ is ethyl, $R_2$ is hydrogen and n is 1.

45. In the method of claim 43 in which R is 1,2-dibromoethyl, $R_1$ is ethyl, $R_2$ is hydrogen and n is 1.

46. In the method according to claim 25 in which said antidote compound has the formula wherein R is haloalkyl, $R_1$ is lower alkyl, $R_5$ is lower alkyl, $R_2$, $R_3$, $R_4$ and $R_6$ are each hydrogen and n is 1.

47. In the method of claim 46 in which R is dichloromethyl, $R_1$ is ethyl, $R_2$ is hydrogen, $R_5$ is methyl and n is 1.

48. In the method according to claim 25 in which said antidote compound has the formula wherein R is haloalkyl, $R_1$ is lower alkyl, $R_5$ is lower alkyl, $R_2$, $R_3$, $R_4$ and $R_6$ are each hydrogen and n is 2.

49. In the method of claim 48 in which R is dichloromethyl, $R_1$ is ethyl, $R_2$ is hydrogen, $R_5$ is methyl and n is 2.

50. The method of protecting a crop from injury due to a thiocarbamate herbicide, comprising applying to the crop seed prior to planting a non-phytotoxic antidotally effective amount of a compound corresponding to the formula

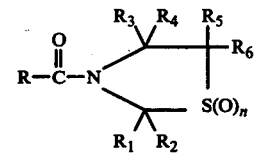

in which R is haloalkyl having 1 to 10 carbon atoms, inclusive, and having 1–3 chloro groups or 1–2 bromo groups, alkyl having 1 to 10 carbon atoms, inclusive, and $R_1$, $R_2$, $R_3$, $R_4$, $R_5$ and $R_6$ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive, and n is an integer having the value of 1 or 2.

51. The method according to claim 50 in which said crop is selected from barley and sorghum.

52. In the method according to claim 51 in which said thiocarbamate herbicide is S-ethyl-dipropylthiocarbamate and the antidote compound has the formula wherein R is dichloromethyl, $R_1$ is methyl, $R_2$ is methyl and $R_3$, $R_4$, $R_5$ and $R_6$ are each hydrogen and n is 2.

53. In the method according to claim 51 in which said thiocarbamate herbicide is S-ethyl-dipropylthiocarbamate and the antidote compound has the formula wherein R is dichloromethyl, $R_1$ is methyl, $R_2$ is methyl and $R_3$, $R_4$, $R_5$ and $R_6$ are each hydrogen and n is 1.

54. The method of protecting a crop from injury due to a thiocarbamate herbicide, comprising preplant incorporation in the soil in which said crop is to be planted, a non-phytotoxic antidotally effective amount of a compound corresponding to the formula

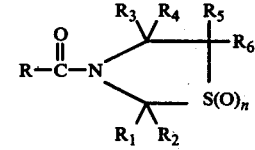

in which R is haloalkyl having 1 to 10 carbon atoms, inclusive, and having 1–3 chloro groups or 1–2 bromo groups, alkyl having 1 to 10 carbon atoms, inclusive, and $R_1$, $R_2$, $R_3$, $R_4$, $R_5$ and $R_6$ are independently selected from the group consisting of hydrogen, lower alkyl having 1 to 4 carbon atoms, inclusive, and n is an integer having the value 1 or 2.

55. In the method according to claim 54 in which said crop is selected from sorghum, wheat, barley and corn.

56. The method of protecting a crop from injury due to a thiocarbamate herbicide, comprising applying to the seed and soil which said crop is to be planted, a nonphytotoxic antidotally effective amount of an antidote compound corresponding to the formula

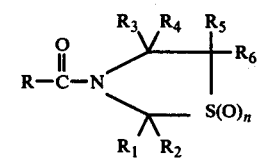

in which R is haloalkyl having 1 to 10 carbon atoms, inclusive, and having 1–3 chloro groups or 1–2 bromo groups, alkyl having 1 to 10 carbon atoms, inclusive, and $R_1$, $R_2$, $R_3$, $R_4$, $R_5$ and $R_6$ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive, and n is an integer having the value 1 or 2.

57. The method according to claim 56 in which said antidote compound has the formula wherein R is haloalkyl having 1 to 10 carbon atoms, inclusive, $R_1$ is lower alkyl having 1 to 4 carbon atoms, inclusive, and $R_3$, $R_4$, $R_5$ and $R_6$ are each hydrogen and n is 2.

58. The method according to claim 56 in which said antidote compound has the formula wherein R is haloalkyl, $R_1$ is lower alkyl, $R_2$ is lower alkyl and $R_3$, $R_4$, $R_5$ and $R_6$ are each hydrogen and n is 1.

59. The method according to claim 56 in which said antidote compound has the formula wherein R is haloalkyl, $R_1$ is lower alkyl, $R_2$ is lower alkyl, $R_5$ is lower alkyl, $R_3$, $R_4$ and $R_6$ are each hydrogen and n is 2.

60. The method according to claim 56 in which said antidote compound has the formula wherein R is haloalkyl, $R_1$ is lower alkyl, $R_2$ is lower alkyl, $R_3$, $R_4$, $R_5$ and $R_6$ are each hydrogen and n is 1.

61. The method according to claim 56 in which said antidote compound has the formula wherein R is haloalkyl, $R_1$ is lower alkyl, $R_2$, $R_3$, $R_4$, $R_5$ and $R_6$ are each hydrogen and n is 2.

62. The method according to claim 56 in which said antidote compound has the formula wherein R is haloalkyl, $R_1$ is lower alkyl, $R_2$, $R_3$, $R_4$, $R_5$ and $R_6$ are each hydrogen and n is 1.

63. The method according to claim 56 in which said antidote compound has the formula wherein R is haloalkyl, $R_1$ is lower alkyl, $R_5$ is lower alkyl, $R_2$, $R_3$, $R_4$ and $R_6$ are each hydrogen and n is 1.

64. The method according to claim 56 in which said antidote compound has the formula wherein R is haloalkyl, $R_1$ is lower alkyl, $R_5$ is lower alkyl, $R_2$, $R_3$, $R_4$ and $R_6$ are each hydrogen and n is 2.

65. An herbicidal composition comprising an active herbicide thiocarbamate and an antidote compound therefor corresponding to the formula

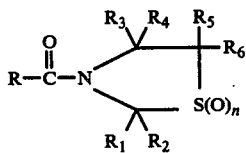

in which R is haloalkyl having 1 to 10 carbon atoms, inclusive, and having 1–3 chloro groups or 1–2 bromo groups, alkyl having 1 to 10 carbon atoms, inclusive, and $R_1$, $R_2$, $R_3$, $R_4$, $R_5$ and $R_6$ are independently selected from the group consisting of hydrogen, lowr alkyl having 1 to 4 carbon atoms, inclusive, alkoxyalkyl having a total of 2 to 4 carbon atoms, inclusive, and lower alkylol having 1 to 4 carbon atoms, inclusive, and n is an integer having the value 1 or 2.

66. The herbicidal composition according to claim 65 in which said antidote compound has the formula wherein R is haloalkyl containing 1 to 10 carbon atoms, inclusive, $R_1$ is lower alkyl containing 1 to 4 carbon atoms, inclusive, $R_2$ is lower alkyl containing 1 to 4 carbon atoms, inclusive, and $R_3$, $R_4$, $R_5$ and $R_6$ are each hydrogen and n is 2.

67. The herbicidal composition of claim 66 in which R is dichloromethyl, $R_1$ is methyl, $R_2$ is methyl and n is 2.

68. The herbicidal composition of claim 66 in which R is chloromethyl, $R_1$ is methyl, $R_2$ is methyl and n is 2.

69. The herbicidal composition of claim 66 in which R is 1,1-dichloroethyl, $R_1$ is methyl, $R_2$ is methyl and n is 2.

70. The herbicidal composition of claim 66 in which R is 2-chloroethyl, $R_1$ is methyl, $R_2$ is methyl and n is 2.

71. The herbicidal composition of claim 65 in which said antidote compound has the formula wherein R is haloalkyl, $R_1$ is lower alkyl, $R_2$ is lower alkyl and $R_3$, $R_4$, $R_5$ and $R_6$ are each hydrogen and n is 1.

72. The herbicidal composition of claim 71 in which R is dichloromethyl, $R_1$ is methyl, $R_2$ is methyl and n is 1.

73. The herbicidal composition of claim 71 in which R is 1,1-dichloroethyl, $R_1$ is methyl, $R_2$ is methyl and n is 1.

74. The herbicidal composition of claim 71 in which R is 2-chloroethyl, $R_1$ is methyl, $R_2$ is methyl and n is 1.

75. The herbicidal composition of claim 65 in which said antidote compound has the formula wherein R is haloalkyl, $R_1$ is lower alkyl, $R_2$ is lower alkyl, $R_5$ is lower alkyl, $R_3$, $R_4$ and $R_6$ are each hydrogen and n is 2.

76. The herbicidal composition of claim 75 in which R is dichloromethyl, $R_1$ is methyl, $R_2$ is methyl, $R_5$ is methyl and n is 2.

77. The herbicidal composition according to claim 65 in which said antidote compound has the formula wherein R is haloalkyl, $R_1$ is lower alkyl, $R_2$ is lower alkyl, $R_3$, $R_4$, $R_5$ and $R_6$ are each hydrogen and n is 1.

78. The herbicidal composition of claim 77 in which R is dichloromethyl, $R_1$ is methyl, $R_2$ is methyl and n is 1.

79. The herbicidal composition according to claim 65 in which said antidote compound has the formula wherein R is haloalkyl, $R_1$ is lower alkyl, $R_2$, $R_3$, $R_4$, $R_5$ and $R_6$ are each hydrogen and n is 2.

80. The herbicidal composition of claim 79 in which R is dichloromethyl, $R_1$ is ethyl, $R_2$ is hydrogen and n is 2.

81. The herbicidal composition of claim 79 in which R is chloromethyl, $R_1$ is ethyl, $R_2$ is ethyl and n is 2.

82. The herbicidal composition of claim 79 in which R is 1,2-dibromoethyl, $R_1$ is ethyl, $R_2$ is hydrogen and n is 2.

83. The herbicidal composition according to claim 65 in which said antidote compound has the formula wherein R is haloalkyl, $R_1$ is lower alkyl, $R_2$, $R_3$, $R_4$, $R_5$ and $R_6$ are each hydrogen and n is 1.

84. The herbicidal composition of claim 83 in which R is dichloromethyl, $R_1$ is ethyl, $R_2$ is hydrogen and n is 1.

85. The herbicidal composition of claim 83 in which R is 1,2-dibromoethyl, $R_1$ is ethyl, $R_2$ is hydrogen and n is 1.

86. The herbicidal composition according to claim 65 in which said antidote compound has the formula wherein R is haloalkyl, $R_1$ is lower alkyl, $R_5$ is lower alkyl, $R_2$, $R_3$, $R_4$ and $R_6$ are each hydrogen and n is 1.

87. The herbicidal composition of claim 86 in which R is dichloromethyl, $R_1$ is ethyl, $R_2$ is hydrogen, $R_5$ is methyl and n is 1.

88. The herbicidal composition according to claim 65 in which said antidote compound has the formula wherein R is haloalkyl, $R_1$ is lower alkyl, $R_5$ is lower alkyl, $R_2$, $R_3$, $R_4$ and $R_6$ are each hydrogen and n is 2.

89. The herbicidal composition of claim 88 in which R is dichloromethyl, $R_1$ is ethyl, $R_2$ is hydrogen, $R_5$ is methyl and n is 2.

* * * * *